US010512819B2

(12) United States Patent
Kow et al.

(10) Patent No.: US 10,512,819 B2
(45) Date of Patent: Dec. 24, 2019

(54) GAIT MONITOR AND A METHOD OF MONITORING THE GAIT OF A PERSON

(71) Applicant: WELL BEING DIGITAL LIMITED, Hong Kong (HK)

(72) Inventors: Ping Kow, Hong Kong (HK); Ming Yip Wallace Wong, Hong Kong (HK)

(73) Assignee: Well Being Digital Limited, Hong Kong (HK)

( * ) Notice: Subject to any disclaimer, the term of this patent is extended or adjusted under 35 U.S.C. 154(b) by 413 days.

(21) Appl. No.: 14/770,053

(22) PCT Filed: Aug. 18, 2015

(86) PCT No.: PCT/CN2015/087316
§ 371 (c)(1),
(2) Date: Aug. 24, 2015

(87) PCT Pub. No.: WO2016/029803
PCT Pub. Date: Mar. 3, 2016

(65) Prior Publication Data
US 2016/0263437 A1  Sep. 15, 2016

(30) Foreign Application Priority Data
Aug. 26, 2014  (HK) .................... 14108707.1

(51) Int. Cl.
*A63B 24/00*  (2006.01)
*A61B 5/11*  (2006.01)
*A61B 5/00*  (2006.01)

(52) U.S. Cl.
CPC .......... *A63B 24/0062* (2013.01); *A61B 5/112* (2013.01); *A61B 5/681* (2013.01);
(Continued)

(58) Field of Classification Search
CPC ....... A61B 5/112; A61B 5/681; A61B 5/6815; A61B 5/6817; A61B 2560/0214;
(Continued)

(56) References Cited

U.S. PATENT DOCUMENTS

| 5,425,378 A | * | 6/1995 | Swezey | ................ | A61B 5/1071 600/587 |
| 6,063,046 A | * | 5/2000 | Allum | .................. | A61B 5/1036 600/595 |

(Continued)

FOREIGN PATENT DOCUMENTS

| CN | 1931090 A | 3/2007 |
| CN | 101394788 A | 3/2009 |

(Continued)

OTHER PUBLICATIONS

Jarchi, Delaram & Wong, Charence & Kwasnicki, Richard & Heller, Ben & Tew, Garry & Yang, Guang. Gait Parameter Estimation From a Miniaturized Ear-Worn Sensor Using Singular Spectrum Analysis and Longest Common Subsequence, .2014, Biomedical Engineering, IEEE Transactions on. 61. 1261-1273. 10.1109/TBME.2014.22997.*

(Continued)

*Primary Examiner* — Corbett B Coburn
(74) *Attorney, Agent, or Firm* — Ware, Fressola, Maguire & Barber LLP

(57) ABSTRACT

A gait monitor 100 is disclosed which has a pair of movement sensors 501, 503 configured to be placed on either side of a user's head, preferably secured in the ears. Therefore, the movement sensors 501, 503 are each placed on both sides of the user's body but in equal distance to the midsagittal plane of the user and can monitor the gait of the user without need of any movement sensor centrally aligned in the midsagittal plane. Furthermore, the gait monitor 100 is able to determine if the steps of the user strikes the ground (Continued)

in a heel strike or forefoot strike in order to help the user improve his running efficiency.

12 Claims, 18 Drawing Sheets

(52) U.S. Cl.
CPC .......... *A61B 5/6815* (2013.01); *A61B 5/6817* (2013.01); *A61B 2560/0214* (2013.01); *A61B 2562/0219* (2013.01); *A61B 2562/04* (2013.01); *A63B 2220/40* (2013.01); *A63B 2220/836* (2013.01)

(58) Field of Classification Search
CPC ........ A61B 2562/0219; A61B 2562/04; A63B 24/0062; A63B 2220/40; A63B 2220/836
USPC ........................................................ 434/236
See application file for complete search history.

(56) References Cited

U.S. PATENT DOCUMENTS

| | | | |
|---|---|---|---|
| 8,784,274 B1 | 7/2014 | Chuang | |
| 2003/0088294 A1* | 5/2003 | Gesotti | A61N 1/36003 607/45 |
| 2005/0177929 A1* | 8/2005 | Greenwald | A42B 3/046 2/425 |
| 2006/0100546 A1* | 5/2006 | Silk | A61B 5/1038 600/592 |
| 2007/0062279 A1 | 3/2007 | Chan et al. | |
| 2007/0118043 A1* | 5/2007 | Oliver | A61B 5/0245 600/519 |
| 2008/0068559 A1* | 3/2008 | Howell | G01C 22/006 351/158 |
| 2008/0082025 A1 | 4/2008 | Hughes et al. | |
| 2008/0258921 A1 | 10/2008 | Woo | |
| 2009/0030350 A1* | 1/2009 | Yang | A61B 5/1038 600/595 |
| 2009/0234614 A1* | 9/2009 | Kahn | G02C 11/10 702/141 |
| 2009/0260426 A1* | 10/2009 | Lieberman | A61B 5/1036 73/65.01 |
| 2010/0117837 A1* | 5/2010 | Stirling | A61B 5/1127 340/573.1 |
| 2011/0184225 A1* | 7/2011 | Whitall | A63B 24/0003 600/28 |
| 2012/0035509 A1* | 2/2012 | Wilson | A61B 5/1038 600/592 |
| 2012/0071743 A1* | 3/2012 | Todorov | G06F 19/3481 600/372 |
| 2012/0072166 A1* | 3/2012 | Keal | G01C 21/165 702/150 |
| 2012/0191229 A1 | 7/2012 | Woo et al. | |
| 2012/0229248 A1* | 9/2012 | Parshionikar | G08B 21/06 340/3.1 |
| 2013/0083009 A1* | 4/2013 | Geisner | G06T 19/006 345/419 |
| 2013/0110010 A1* | 5/2013 | Fuke | A61B 5/1117 600/595 |
| 2013/0172691 A1* | 7/2013 | Tran | A61B 8/488 600/301 |
| 2013/0178958 A1* | 7/2013 | Kulach | A63B 24/0021 700/91 |
| 2013/0278435 A1* | 10/2013 | Ellis | A43B 1/0054 340/870.07 |
| 2014/0025361 A1* | 1/2014 | Greene | G16H 50/30 703/11 |
| 2014/0031703 A1* | 1/2014 | Rayner | A61B 5/02055 600/484 |
| 2014/0031725 A1 | 1/2014 | Jeon | |
| 2014/0066816 A1* | 3/2014 | McNames | A61B 5/002 600/595 |
| 2014/0156215 A1* | 6/2014 | Eastman | A61B 5/112 702/141 |
| 2014/0163704 A1* | 6/2014 | DePietro | A43B 3/0005 700/91 |
| 2014/0180171 A1* | 6/2014 | Hyde | A61B 5/002 600/595 |
| 2014/0194702 A1* | 7/2014 | Tran | A61B 8/06 600/301 |
| 2014/0204021 A1* | 7/2014 | Sugihara | G06F 3/012 345/156 |
| 2014/0228649 A1* | 8/2014 | Rayner | A61B 5/1118 600/301 |
| 2014/0282877 A1* | 9/2014 | Mahaffey | H04L 63/0853 726/3 |
| 2015/0112603 A1* | 4/2015 | Zhong | G06K 9/46 702/19 |
| 2015/0164377 A1* | 6/2015 | Nathan | A61B 5/1122 600/595 |
| 2015/0185518 A1* | 7/2015 | Igarashi | G02F 1/1334 349/12 |
| 2015/0326570 A1* | 11/2015 | Publicover | G06F 21/64 726/4 |
| 2015/0351690 A1* | 12/2015 | Toth | A61B 5/6833 600/373 |
| 2016/0054876 A1* | 2/2016 | Robison | H04L 43/0876 715/772 |
| 2016/0114213 A1* | 4/2016 | Lee | A61B 5/6802 434/255 |
| 2016/0256082 A1* | 9/2016 | Ely | A61B 5/0024 |
| 2016/0262687 A1* | 9/2016 | Vaidyanathan | A61B 5/7264 |
| 2016/0287166 A1* | 10/2016 | Tran | H04B 1/3827 |
| 2016/0310341 A1* | 10/2016 | Yu | G09B 5/02 |
| 2016/0337863 A1* | 11/2016 | Robinson | H04W 12/08 |
| 2017/0206691 A1* | 7/2017 | Harrises | G06T 11/60 |
| 2017/0258370 A1* | 9/2017 | Plotnik-Peleg | A61B 5/1104 |
| 2017/0281085 A1* | 10/2017 | Lee | A61B 5/6802 |
| 2017/0323485 A1* | 11/2017 | Samec | G06F 3/013 |
| 2017/0372055 A1* | 12/2017 | Robinson | H04W 12/06 |

FOREIGN PATENT DOCUMENTS

| | | |
|---|---|---|
| CN | 101695445 A | 4/2010 |
| CN | 103083025 A | 5/2013 |
| CN | 103728874 A | 4/2014 |
| JP | 2005118402 A | 5/2005 |
| WO | 2014108948 A | 7/2014 |
| WO | 2014089238 A | 12/2014 |

OTHER PUBLICATIONS

Extended European Search Report, Application 157481157.3-1657 / 3010414 PCT/CN2015087316, dated Dec. 14, 2016, 8 pages.
Search Report, Hong Kong Short Term Patent Application, HK1400289, dated Sep. 26, 2014, 6 pages.
International Seach Report (ISR), PCT/CN2015/087316, 3 pages.
English Abstract, CN103728874A , 2 pages, Pub date: Apr. 2014.
English Abstract, JP2005118402A , 2 pages, Pub date: May 2005.
English Abstract, CN101695445A , 2 pages, Pub date: Apr. 2010.

\* cited by examiner

GAIT MONITOR AND A METHOD OF MONITORING THE GAIT OF A PERSON

FIELD OF THE INVENTION

This invention relates to devices for monitoring the gait of a person, particularly devices for monitoring gait of a runner.

BACKGROUND

Correct posture of the body is important to avoid stiffness and injury as one goes about his daily affairs. Therefore, it has been proposed to use electronic devices to monitor posture and to provide feedback for posture correction. In many of such devices, at least one accelerometer is used to monitor the posture in real time. U.S. Pat. No. 5,749,838 (Kline) discloses such a posture monitoring device which is attached to the back of a user by a belt and which is aligned to the user's midsagittal plane. The midsagittal plane is defined as an imaginary vertical plane which cuts centrally through a user's body from the back to front. The device can be attached to the level of the L4-L5 vertebrae or the S1-S2 vertebrae. Any change in curvature of the backbone within the midsagittal plane can be detected by the accelerometer in the device. The user's average pelvic angle as captured when he was walking is taken as the reference for good posture. Subsequently, the user is considered as adopting a good standing posture if his pelvic tilt falls within +/−5° of this average pelvic angle when he is standing. If the posture is detected to be bad, the device vibrates to alert the user of his bad posture.

Kline's device is unable to monitor the gait of the user when he is walking and running. However, it is just as important to runners to monitor their posture and gait in order to avoid injury and to improve running efficiency. In particular, Kline's device cannot monitor the balance between the user's left and right sides; postural analysis is entirely along the curvature of the spine towards the front or back of the user. Therefore, in other such devices, multiple sensors are used to monitor gait. In one example, an inertial sensor or accelerometer placed in a belt tied around the waist of a user is vertically aligned to his navel, which is the body's lateral centre, to monitor the midsagittal plane. Another sensor unit is tied around the chest of the user, also aligned to his navel. The ankles and wrists are also tied with a sensor unit each. Together, these sensor units measure characteristics of the gait of the user, such as dynamic mobility, including cadence, stride velocity, stride length, trunk rotation, turning duration and arm swing velocity. In particular, the centrally placed sensor units are able to monitor any lateral skew of force the user's steps and to determine if his gait is laterally balanced.

However, all these devices require the user to wear a belt or harness by which at least one sensor unit is positioned in his midsagittal plane, either on his chest or near his navel. Monitoring of lateral balance in gait becomes inaccurate if the sensor unit is displaced into misalignment to the user's navel. Unfortunately, it is difficult to maintain alignment of a sensor unit to the navel if the user is performing an exercise; movements of the user tend to rotate the belt about him. Therefore, these devices are not rugged enough to monitor a user's posture and gait accurately during rigorous and prolonged exercises, such as long distance running.

Accordingly, it is desirable to provide a device which is able to monitor the gait of a runner, and which has a possibility of mitigated risk of inaccuracy due to displacement of the device during exercise.

SUMMARY OF THE INVENTION

In a first aspect, the invention proposes a gait monitor comprising a pair of movement sensors, wherein the movement sensors are configured to be worn on the left and right sides of a user's body respectively and to monitor force patterns in the steps of the user.

"Movement sensors" include all manner of sensors which can monitor parameters such as velocity, acceleration, distance displacement, angular changes and so on, particularly parameters which can be used to obtain or deduce force patterns in the steps of the user. These movement sensors are typically accelerometers or gyroscopes.

Due to the natural symmetry of the body, the invention provides the possibility of placing each movement sensor on the same but laterally opposite points on the user's body, such as his hips, his temples or his ears, and provides that the movement sensors can be placed across and equidistance to the midsagittal plane of the user. In the same distance from the midsagittal plane of the use, the pair of movement sensors on either side of this body can deduce the same information which is obtainable by a navel aligned movement sensor. The pair of movement sensors can therefore be used to monitor forces applied in the left and right steps of the user during running or walking to determine lateral balance in gait without the likelihood of being misaligned to the midsagittal plane of the user.

Relative one to the other, these left and right sides of the user's body are typically incapable of independent movements. These parts of the body are usually located on the head or the trunk, and not in the limbs. These left and right parts of the body move generally in tandem, together, or one about the other in rotation, and do not move away or apart from the other in different directions. Such parts of the human body which is generally or roughly incapable of moving independently, away or apart from the opposite counterparts are those such as the ears, the temples, left-right opposite positions on the jaw bone, left-right opposite positions on forehead, left-right opposite positions on the pelvis, hip bones, chest or ribs, teeth on the opposite sides of the jaw, the opposite corners of both eyes and so on.

It may be possible that some individual persons may exercise such body parts to be able to move one independently of the counterpart one, such as moving one ear and not the other, but this is an exception rather than the norm in normal body movements. These mirrored movements between any such two parts provide a possibility of deducing the movements of a point or plane located in a plane of symmetry between the parts.

Some body parts such as the ears are capable of being moved along when the head tilts or turn. This may add additional readings to the movements detected from the user's gait. However, as both ears move together, use of two movement sensors makes it possible to identify movements resulting entirely from head tilting or turning, and allows one to negate their resultant readings by the movement sensors. In this way, any movements detected on any two of such counterparts which are generally incapable of relative motions may be used to monitor if a person has a tendency to skew towards one side of his body in the general.

In contrast, either one of limbs such as the hands, wrists or feet is capable of moving and flailing independently one of the other. For example, one hand may flail upwardly while the other hand downwardly. If the pair of movement sensors are placed on the user's feet or hands, the readings obtained by these movement sensors will be unusable to estimate the skew of the midsagittal plane of the user, and therefore cannot measure gait as a matter of vertical misalignment or skew.

Preferably, the gait monitor comprises a structure suitable for being worn on the user's head, and the movement sensors are arranged in the gait monitor such that the movement sensors are positioned on the opposite sides of the user's head when the gait monitor is worn. More preferably, the movement sensors are configured by being arranged in the gait monitor such that the movement sensors are attached to the user's ears when the gait monitor is worn on the user's head. Being "attached" to the ear includes any way of securing the movement sensors to the ear. For example, the movement sensors can be configured to be worn in the user's ears in the same way as earphones or clipped on the user's ears in the same way as hearing aids. Alternatively, the gait monitor can be configured as a headphone having earpieces installed with movement sensors. Yet alternatively, the gait monitor is a spectacle frame, and the movement sensors are arranged into the temples of the spectacle frame to be near the ear when the spectacle frame is worn.

The position of the ear is relatively precise compared to some other parts of the body due to the small definable area of the ear. Furthermore, the sides of the head are unlike joints or the trunk of a body which are subject to bending movements. Configuring the movement sensors to be suitable for being attached to the ears improves repeatability of the movement sensor positions. Furthermore, it is also common practice to wear a headgear such as earphones when one is running or exercising and it will not be considered odd like wearing a chest harness attached with a movement sensor.

Preferably, the gait monitor is configured to be able to compare the force patterns in the steps of each the user's legs. That is, the two movement sensors can be used to detect the left foot cycle and right foot cycle separately, and precisely trace the landing pattern of each leg. Any uneven application of force between the left and right leg indicates that the user's gait is imbalanced laterally.

Accordingly, the invention provides a possibility of dispensing away with the need to carefully align a movement sensor to the navel, or in the midsagittal plane, and mitigates the risk of misaligning a movement sensor to the navel. A relatively rugged gait monitor is therefore possible, one which is suitable for monitoring the gait of the user accurately in an exercise such as running.

Preferably, the gait monitor is configured to detect force pattern in the steps of the use, particularly to determine if the steps land on the ground by a heel strike or by a forefoot strike. Typically, the force pattern of each step is traced from the time the user's foot leaves the ground, through to the moment when his foot re-engages the ground and up to the moment when his foot leaves the ground again. The gait monitor can be used to help a user who wants to monitor and cut his habit of heel striking on the ground when he runs.

In a second aspect, the invention proposes a method of monitoring the gait of a user, comprising the steps of: attaching a first movement sensor to the left side of the user and attaching a second movement sensor on the corresponding right side of the user, such that the first and second movement sensors are equidistance to the midsagittal plane of the user; and monitoring each foot of the user using the movement sensor on the respective side of the user to obtain force pattern of the steps of each foot.

In a third aspect, the invention proposes an audio headphone comprising two earpieces; the ear pieces each installed with a movement sensor for detecting the force pattern of the steps of the wearer of the headphone. In the prior art, no headphones which can be used to play music has a dual function including one for monitoring the gait of a user. The invention therefore provides a gait monitor in the form of a headphone which does not have a central sensor unit to be aligned to the navel of the wearer which yet obtaining the same gait information and possibly more.

In a fourth aspect, the invention proposes an ear mountable movement sensor configured to monitor force patterns in the steps of the user. The ear mountable movement sensor can be in the form of an earplug, an ear phone or another device attachable to the ear. Providing the mountable movement sensor singularly allows the user to obtain separate mountable movement sensor from different suppliers, or to replace any one mountable movement sensor of a pair which is damaged. This is advantageous over prior art which requires the user of any ear mount-able device to be bought in a pair and to be replaced as a pair in case of damage to either one of the devices in the pair.

In a fifth aspect, the invention proposes a device comprising: a pair of movement sensors, each one of the pair of movement sensors configured to be placed apart from the other to monitor the difference in acceleration detected by each of the movement sensors; wherein the difference is useable an indication of the device being tilted.

Preferably, the movement sensors are powered by energy harvested from a person wearing the device.

Preferably, the device is capable of being strapped to the wrist of a user, such as a smart watch with a user interactive screen. The pair of movement sensors allows the smart watch to sense the tilting of the screen to determine if the screen is generally level to the ground, and then displaying incoming messages and other information on the screen. Conversely, this prevents the same information from being displayed on the screen if the screen is detected to be generally perpendicular to the ground, reducing accidental disclosure of information to a person standing nearby.

More preferably, two or more movement sensors are arranged on the edge of the face of the watch with a distance between the two movement sensors, or over any distance on the surface of the watch, or even across any two points on the watch strap. In particular, having more than two movement sensors allows the possibility of the malfunction of any one of the movement sensors without causing the entire tilt monitoring function to breakdown.

More preferably, a movement sensor is also placed centrally in the plane of the watch surface. This allows the general movements of the watch to be monitored, against which the readings of the other movement sensors at the edge of the watch, or other eccentrically placed movement sensors, may be referenced.

Although watches have been described, other devices which may benefit from the use of movement sensors are possible, such as gaming joysticks, wirelessly interactive rings or bracelets and so on.

BRIEF DESCRIPTION OF THE DRAWINGS

It will be convenient to further describe the present invention with respect to the accompanying drawings that illustrate possible arrangements of the invention, in which like integers refer to like parts. Other embodiments of the invention are possible, and consequently the particularity of the accompanying drawings is not to be understood as superseding the generality of the preceding description of the invention.

DESCRIPTION OF SPECIFIC EMBODIMENTS

Figure 1:
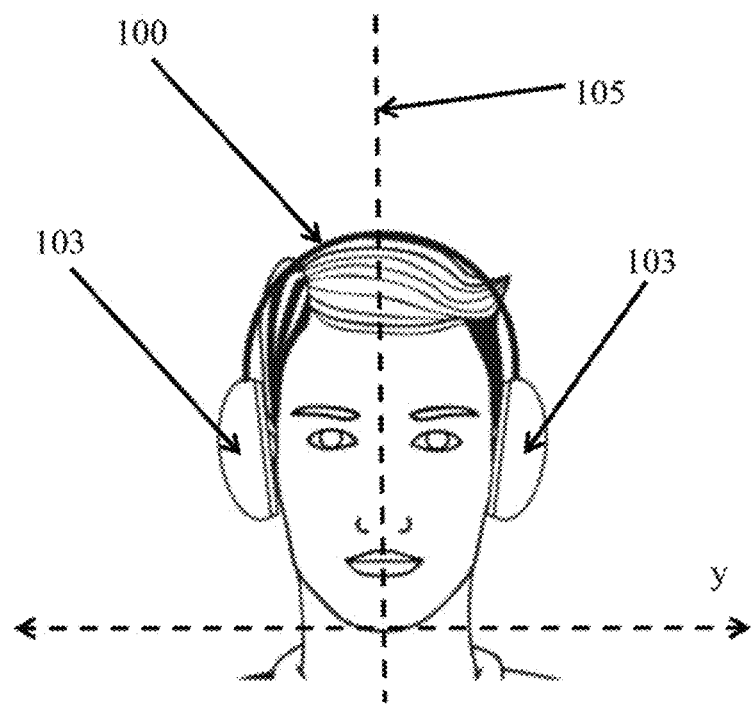
FIG. 1 shows a first embodiment of the invention.

FIG. 1 shows a first embodiment, which comprises a gait monitor 100 in the form of a headphone for wearing on the head of a user. The headphone has earpieces 103 for sitting over each of the user's ear. Inside each earpiece 103 is a movement sensor for detecting movements, such as a 3-axes accelerometer (not visible in FIG. 1). Therefore, each of the two sides of the head of the user is monitored by a movement sensor.

As the skilled man knows, an accelerometer is a device that measures proper acceleration, or g-force. Single- and multi-axis models of accelerometer are available to detect magnitude and direction of the proper acceleration as a vector quantity, which can be used to sense orientation.

Due to the natural symmetry of the human body, the relative location of each movement sensor to the lateral centre of the user is almost the same, whether from the left or the right. In other words, the movement sensors are virtually equidistance to the midsagittal plane 105 of the user. The pair of movement sensors can therefore be used to monitor forces applied in the left and right steps of the user during running or walking to determine lateral balance in gait. There is no need to laboriously align any movement sensor to the user's navel. The same information and more which is obtainable by a navel aligned movement sensor can be obtained by the pair of movement sensors in equidistance to the midsagittal plane 105.

Figure 2:
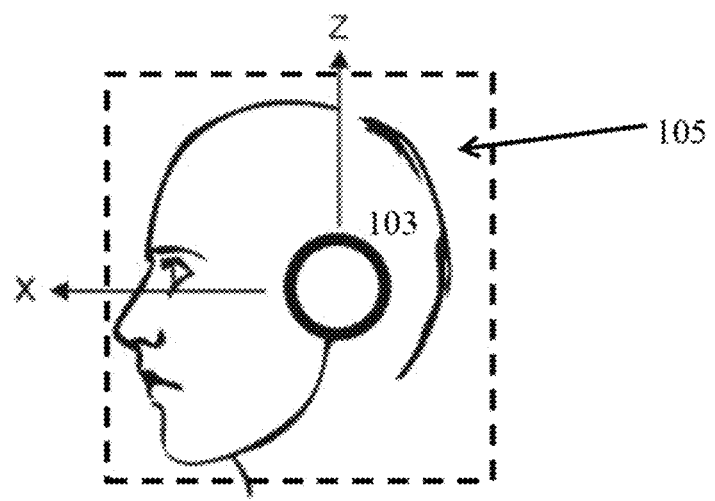
FIG. 2 is a schematic drawing of the first embodiment from a side view.

FIG. 2 is a side view of the user wearing the gait monitor 100. The vertical direction to the ground is the z-axis while the forward direction as the user runs is the x-axis. Not visible in FIG. 2 is the y-axis which is sidewise to the user and extends into the drawing. Therefore, the user's downward and upward forces in a run are detected as force components along the z-axis.

Figure 3:
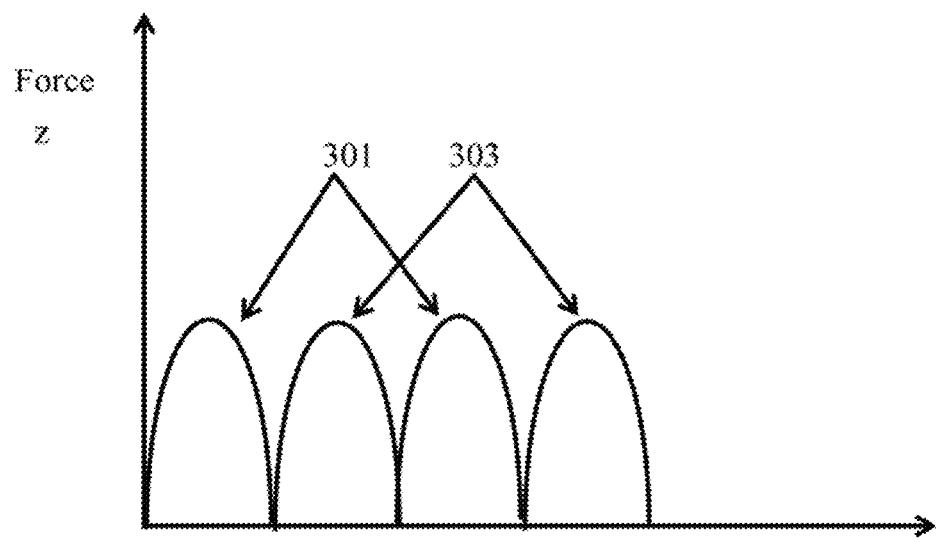
FIG. 3 is a chart showing the balanced gait of a running user as monitored by prior art to the embodiment of FIG. 1.
Figure 4:
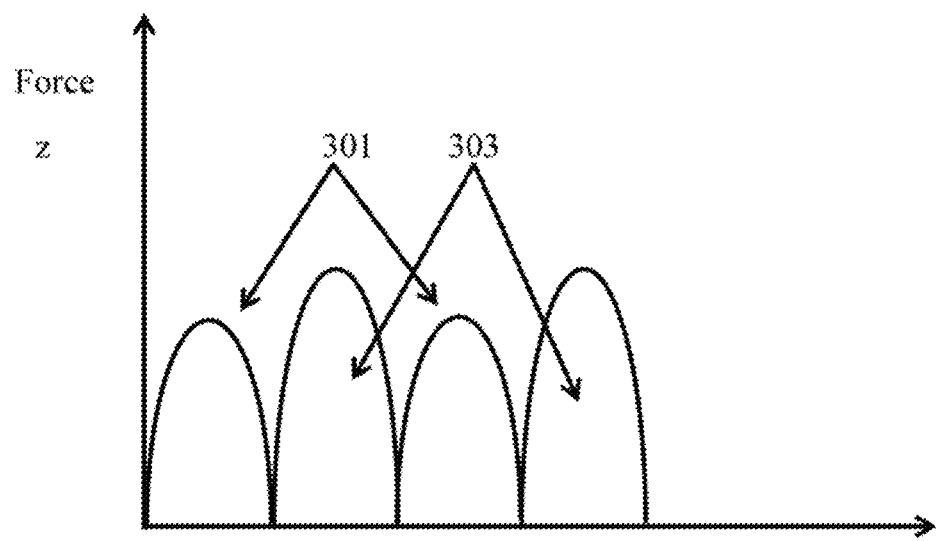
FIG. 4 is a chart showing the imbalanced gait of a running user as monitored by prior art to the embodiment of FIG. 1.

In the prior art, one movement sensor has to be aligned to the midsagittal plane 105 of the user very accurately in order to determine if the user's gait is imbalanced. FIG. 3 and FIG. 4 are comparative data taken from the prior art. FIG. 3 is a chart of the forces along the z-axis detected by such prior art movement sensor over four steps as the user runs. The peaks in FIG. 3 represent in the alternative the steps of the user's left leg 301 and right leg 303. That is, the first peak and the third peak were observed from the left leg 301 and the second peak and the fourth peak were observed from the right leg 303. If the user's left and right steps are in balance, the force which the user applies to his left leg 301 and the force he applies to his right leg 303 should be almost the same in magnitude and shape. FIG. 4 shows what happens if the user's gait is imbalanced. The force which the user applies on the left leg 301 is lesser while the force which he applies on the right leg 303 is greater. In this way, the one movement sensor determines that the user is applying more force on his right leg 303 and the user's gait is imbalanced laterally. However, there is a situation in which it is possible that the chart of FIG. 4 is obtained even if the user is running with a balanced gait. This happens when the movement sensor is placed off centre to the midsagittal plane 105. For example, if the movement sensor is placed a little skewed to the right, the movement sensor will register less force in the user's left steps and more force in the user's right steps, and the movement sensor will report an imbalanced gait incorrectly. In such prior art, the movement sensor is typically secured on a belt to be tied around the waist or the chest of the user. Unfortunately, this allows the belt to rotate about the user's waist or chest as the user runs which displaces the movement sensor from the user's midsagittal plane 105, leading to false readings.

Figure 5:
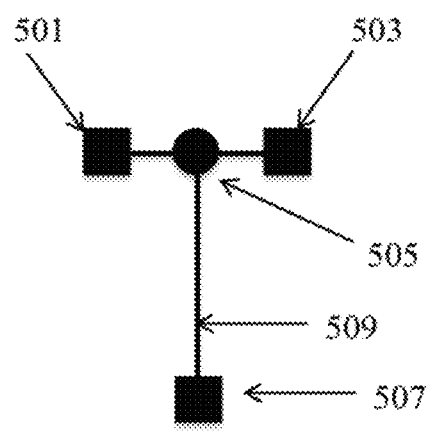
FIG. 5 is a schematic drawing of the mechanism of the first embodiment.

In contrast, the present embodiment 100 does not require a movement sensor to be placed in the midsagittal plane 105 of the user while yet providing accurate measurement of gait balance. FIG. 5 illustrates that in the present embodiment, two movement sensors 501, 503 placed equidistance to a point 505 in a central line 509 are used to obtain the same or similar information as a single movement sensor 507 placed in the same central line. The point 505 between the two movement sensors 501, 503 in this case is equivalent to the centre of the user's head. The other point 507 lower in the central line is equivalent to the navel below the user's head, which is a point used commonly in the prior art for positioning a movement sensor.

Figure 6:
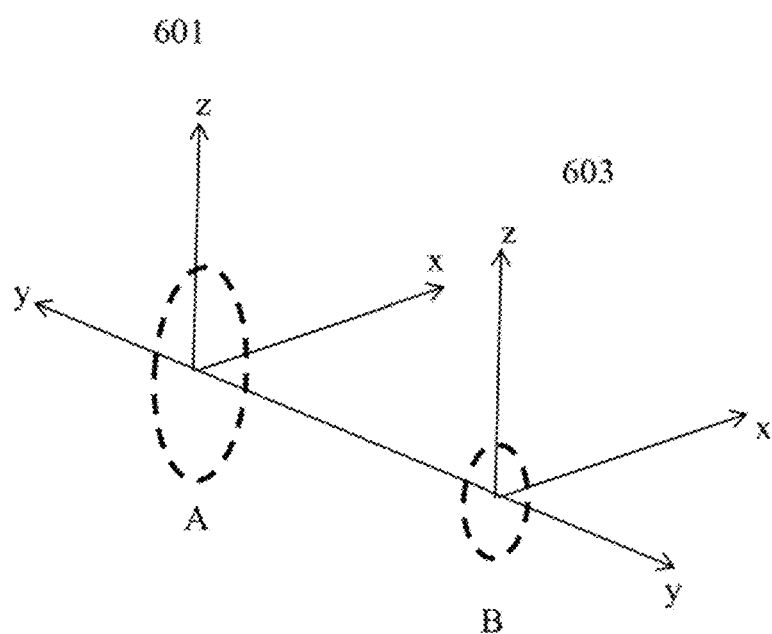
FIG. 6 are illustrations of the force vectors of an imbalanced gait of a running user as monitored by the embodiment of FIG. 1.

FIG. 6 illustrates the forces possibly detected by each of the two movement sensors in the embodiment 100 as the user is running. The circles A and B in FIG. 6 represent the possible distribution of force in the z-axis and y-axis on the user's left 601 and right leg 603 respectively, as the user runs. If the difference of the forces detected between the two movement sensors is significant or large, the user is running with an imbalance gait.

Figure 7:
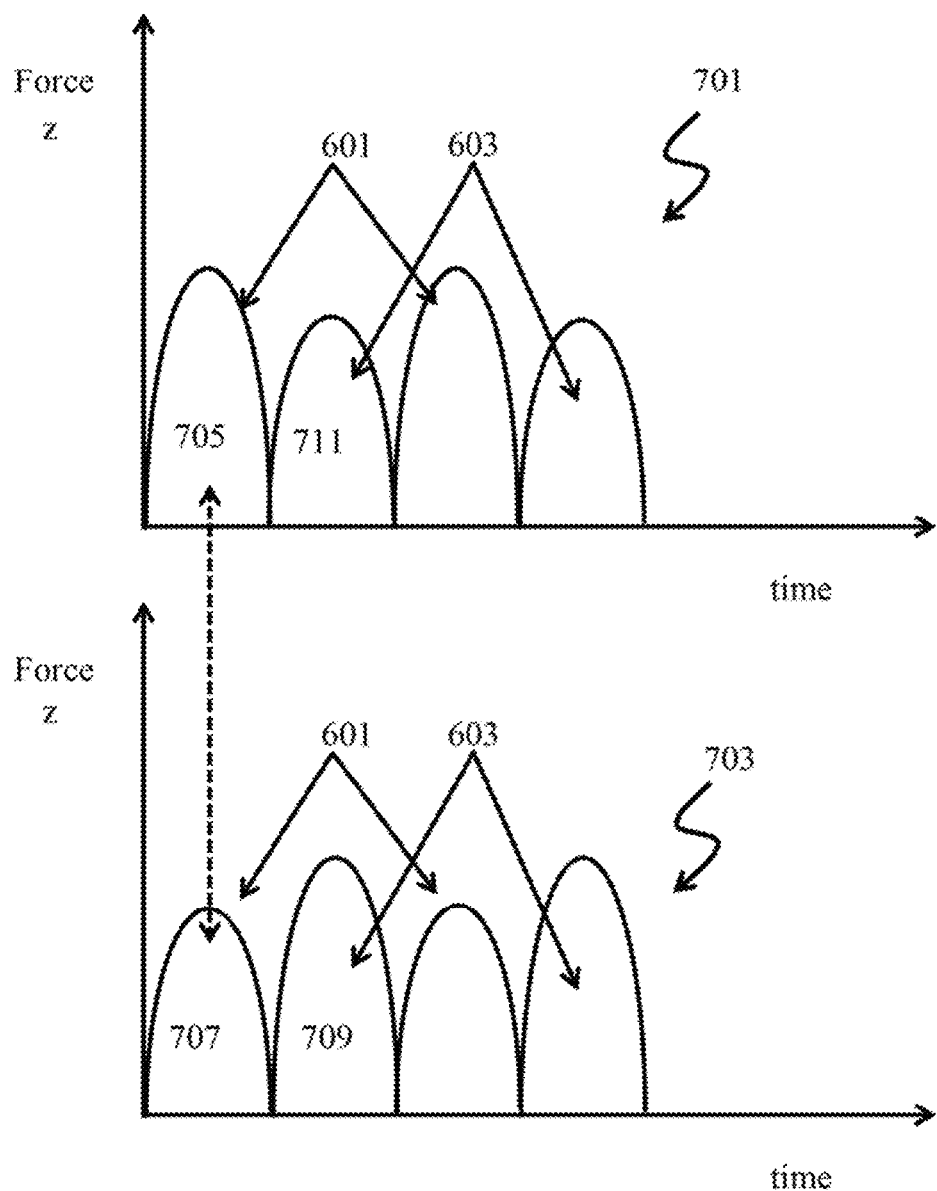
FIG. 7 explains how the first embodiment is capable of determining a gait is balanced.

FIG. 7 shows two charts, the top chart 701 representing the data obtained by the movement sensor in the left side 601 of the gait monitor 100 and the bottom chart 703 representing the data obtained by the acceleration sensor on the right side 603. Both movement sensors detect forces in every step the user makes when he is running. The movement sensor on the left detects a peak with greater magnitude when the user lands on his left leg 601 then the movement sensor on the right. The double headed arrow in broken line points to two peaks labelled 705 and 707 and indicates that these two peaks relate to the same step. Conversely, the movement sensor on the right detects a peak with greater magnitude when the user lands on his right leg 603 than the movement sensor on the left. In order to determine imbalance of gait between the user's left and right sides, the gait monitor 100 compares the first peak 705 in the top chart 701 with the second peak 707 in the bottom chart 703. If the gait of the user is balanced laterally, the second peak 709 in the bottom chart 703 should have the similar magnitude and pattern as the first peak 705 in the top chart 701. The user is running with an imbalanced gait if the difference in magnitude and pattern between the first peak 705 in the top chart 701 and the second peak 709 in the bottom chart 703 is significant. Alternatively, the gait monitor 100 can also compare the first peak 707 in the bottom chart 703 with the second peak 711 in the top chart 701.

To compare the peaks, the gait monitor 100 typically comprises processing capability. The processing capability can be in the form of a microcontroller contained in the gait monitor such as one located in one of the ear pieces 103. Optionally, the microcontroller can be a remote one worn on the belt of the user and to which the gait monitor is hard-wired. Alternatively, the microcontroller can be situated remotely and communicates with the movement sensors wirelessly such as by Bluetooth.

The gait monitor 100 comprises a feedback system for indicating to the user the quality of his gait. In this embodiment, the headphone can be used to provide audible feedback to the user. Advantageously, the headphone can also be connected to a music player such as a CD player to let the user enjoy music when there is no need for audio feedback about the quality of his gait. Alternatively, the feedback system can be a visual one such as a screen on a wireless wristwatch receiving and displaying gait information.

Figure 8:
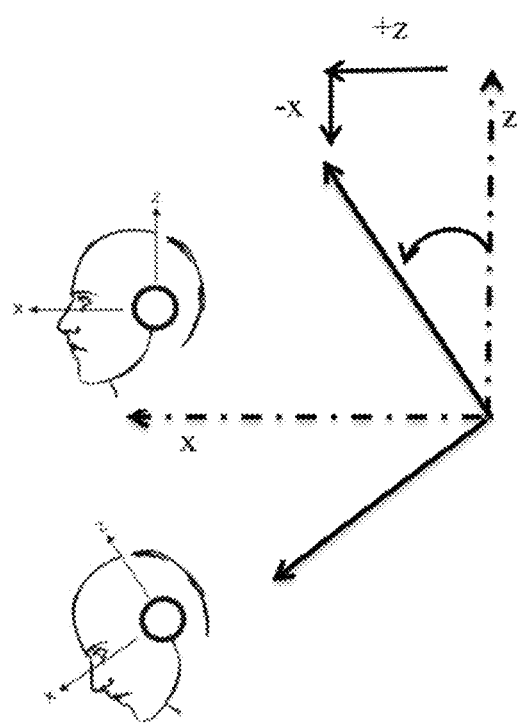
FIG. 8 explains how the first embodiment treats signals due to nodding of the head.

When a user is running, he generally keeps his head steady without nodding or else this gaze on the road will not be steady. However, in the rare event that the user is nodding as he runs, there will be a force component along the z-axis accompanied by a force component in the x-axis concurrently. This is illustrated in FIG. 8, showing how the head is tilted forwardly and downwardly as the head nods. Accordingly, whenever it is observed that there is an increase in force variation along the x-axis accompanied by reduction of force variation along z-axis, the gait monitor 100 will disregard the entire peak 301, 303 in the z-axis by assuming it is contributed by nodding. Skipping the data of one or two such steps will not compromise the overall assessment of the gait of the user.

In any case, the user wears the ear pieces 103, the movement sensors are relatively near the pivot joint of the atlas and axis vertebrae to keep nodding movements affecting the movement sensor readings to a minimal.

Figure 9:
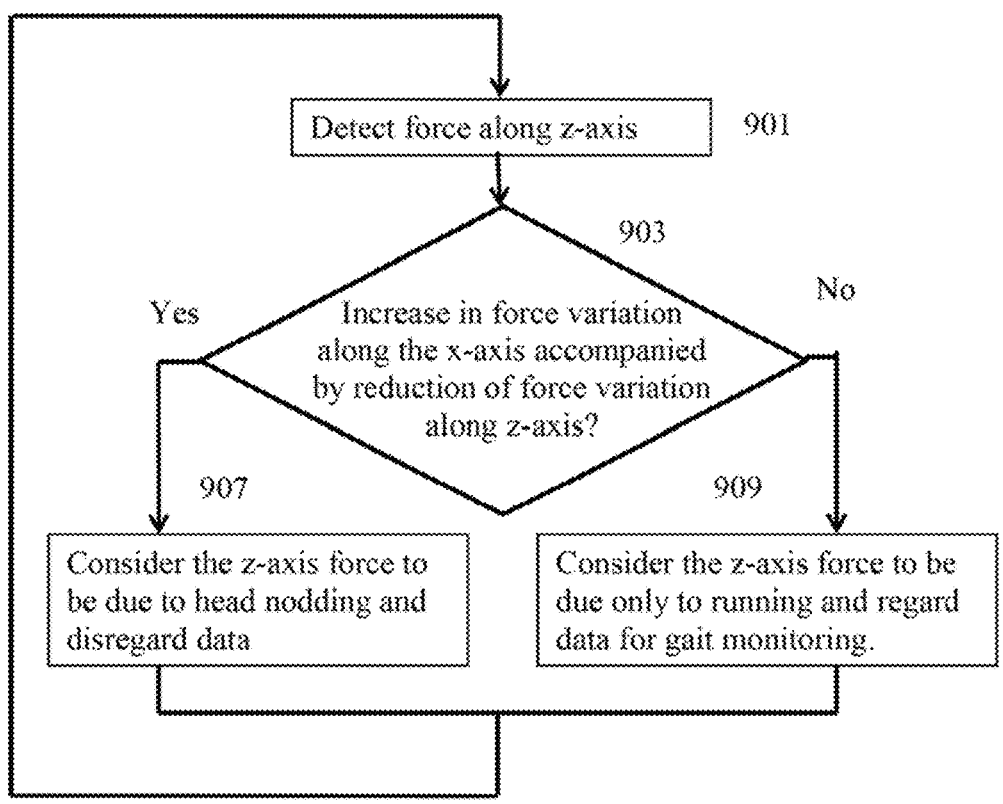
FIG. 9 is a flowchart relating to FIG. 8.
Figure 10:
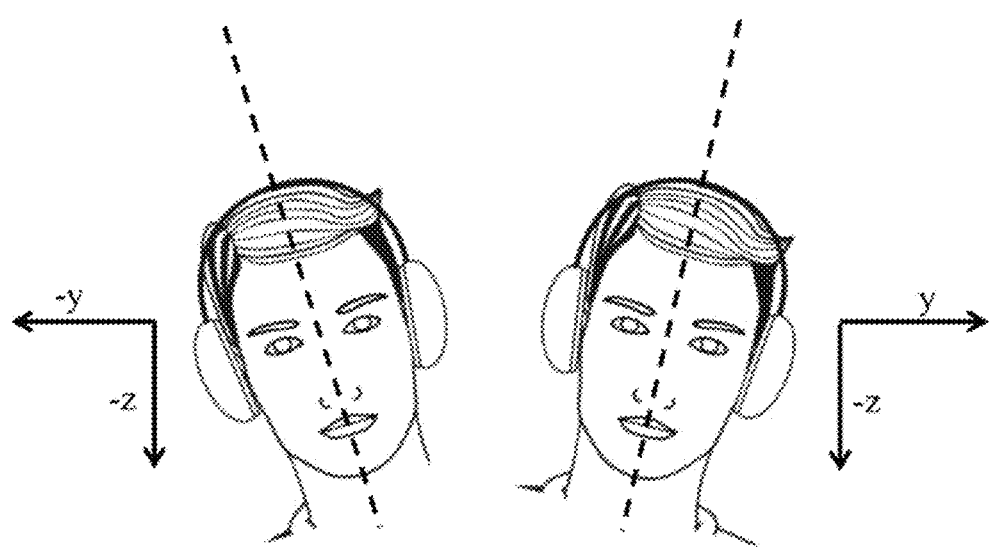
FIG. 10 explains how the first embodiment treats signals due to sidewise tilting of the head.

FIG. 9 is a flow chart showing how the gait monitor 100 determines whether to disregard a peak 301, 303 detected by one of the movement sensors. When a force is detected along the z-axis, at step 901, the gait monitor 100 checks if there is a concurrent force detected along the x-axis, at step 903. As mentioned, if the user nods his head, there will be an increase in force variation along the x-axis accompanied by reduction of force variation along z-axis. In this case, the gait monitor 100 considers the z-axis force to be due to or to have been affected by head nodding and will disregard the z-axis data, at step 907. If there is no concurrent force in the x-axis, the gait monitor 100 considers the z-axis force to be due only to running and will regard the z-axis data for gait monitoring, at step 909. The flowchart then resumes to the earlier step, at step 901 to analyse the next force component detected in the z-axis.

Figure 11:
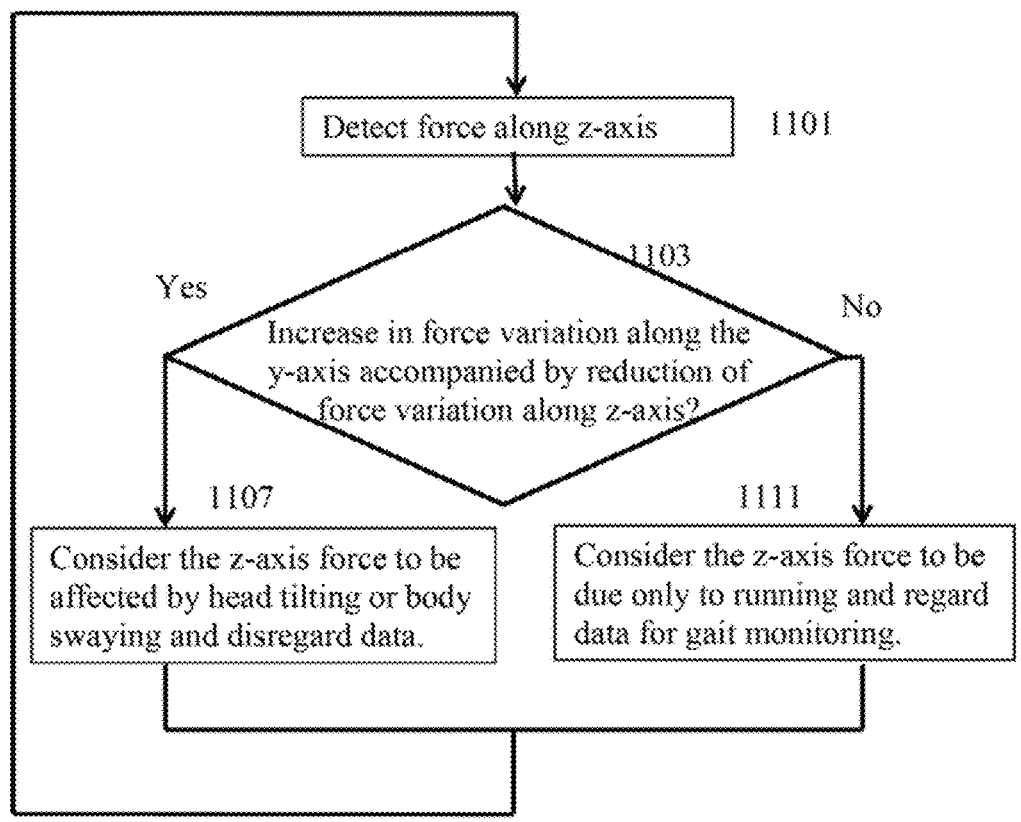
FIG. 11 is a flowchart relating to FIG. 10.

Similarly, tilting of the user's head sidewise will result in forces detected concurrently along the y-axis and the z-axis of both movement sensors. Accordingly, whenever there is a force component along the z-axis which is accompanied by a force component along the y-axis, the gait monitor 100 will disregard the z-axis component by assuming it is affected by the user tilting his head. The same effect is seen when the user sways from side to side. FIG. 11 is a corresponding flow chart showing how the gait monitor 100 determines whether to disregard a peak 301, 303 which may be affected by tilting of the head. When a force is detected along the z-axis, at step 1101, the gait monitor 100 checks if there is a concurrent force detected along the y-axis, at step 1103. As mentioned, if the user tilts his head or sways his body, there will be an increase in force variation along the y-axis accompanied by reduction of force variation along z-axis. In this case, the gait monitor 100 disregards the z-axis data, at step 1107. If there is no concurrent force in the y-axis, the gait monitor 100 considers the z-axis force to be due only to running and will regard the z-axis data for gait monitoring, at step 1111. The flowchart then resumes to the earlier step, at step 1101 to analyse the next force component detected in the z-axis.

Figure 12:
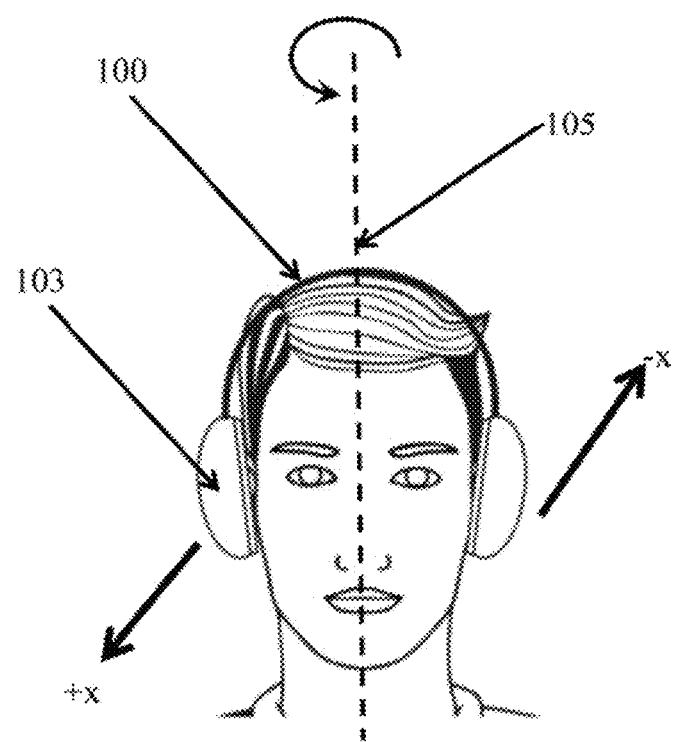
FIG. 12 explains how the first embodiment treats signals due to turning of the head.

When the user turns his head, which is the most common head movement during running, the two movement sensors 501, 503 will detect x-axis force components in opposite directions. This is illustrated in FIG. 12 showing how one movement sensor will detect a negative force component in the x-axis and the other a positive force component in the x-axis. It is optional to disregard any force component in the z-axis which is accompanied by turning movement of the head, as the turning movement does not add false data to the z-axis component. Accordingly, in some embodiments, a two-axes movement sensor can be used to monitor only the z- and x-axes, instead of using a three-axes movement sensor.

A gait monitor 100 has been described which comprises a pair of movement sensors 501, 503, the pair of movement sensors 501, 503 configured to be worn on the left and right sides of a user's body respectively, and the movement sensors 501, 503 configured to detect the force pattern of the steps of the user. The gait monitor (100) does not have a movement sensor centrally situated on a user's body which can be displaced easily. This is because the two movement sensors 501, 503 are not placed in a belt tied to the waist or the chest but is secured to the sides of the user's head. In particular, it is preferred that the two movement sensors 501, 503 are secured into a head mounting device such as the ear pieces 103 of a headphone. More preferably, however, the ear pieces 103 are not ear mugs to be placed over each year but are ear pieces 103 which are insert-able into ear holes.

This ensures that the locations of the movement sensors on the user's head are consistent and repeatable between uses.

Preferably, the embodiment 100 can be connected to a music player such as a compact disc player to allow the user to enjoy music as he performs an exercise. This also provides the possibility that the earphone device can provide an audio reminder to the user to keep a correct body movement when his gait is significantly imbalanced.

The force pattern detected by the movement sensors can be sent wirelessly to an external device such as a mobile phone the runner is carrying for computing or analysis. Alternatively, a processor can be installed in the earphone for performing the computation. All these variations will be known to the skilled man and needs no elaboration here.

The embodiment described can also be used to monitor the manner in which the user's steps land on the ground when running. In general, there are three major ways a runner's foot strikes the ground, by:
1. Heel Striking Heel lands first, then the forefoot comes down (heel-toe running)
2. Midfoot Striking Heel and ball of the foot land simultaneously
3. Forefoot Striking Ball of the foot lands first before the heel comes down (toe-heel-toe running).

In heel striking, the collision of the heel with the ground generates a significant impact with a large force, which sends a shock wave up through the body. In forefoot striking, the collision of the forefoot with the ground generates a minimal impact force. A good foot landing in a run should feel gentle, relaxed and compliant. Therefore, a runner can avoid experiencing a large impact force by forefoot striking. It has been discovered that since the invention of shoes with thick soles and thick heels, most people have habitually adopted heel striking when running, whilst people who tend to go about shoeless or tend to wear shoes with thin soles tend to adopt forefoot striking. Forefoot striking provides the runner a sub-conscious ability of deciding exactly which part of the forefoot and midfoot to land first, allowing the runner to navigate nimbly on uneven and mildly stony grounds. Therefore, forefoot striking is critical for greater running efficiency and for energy economy.

Figure 13:
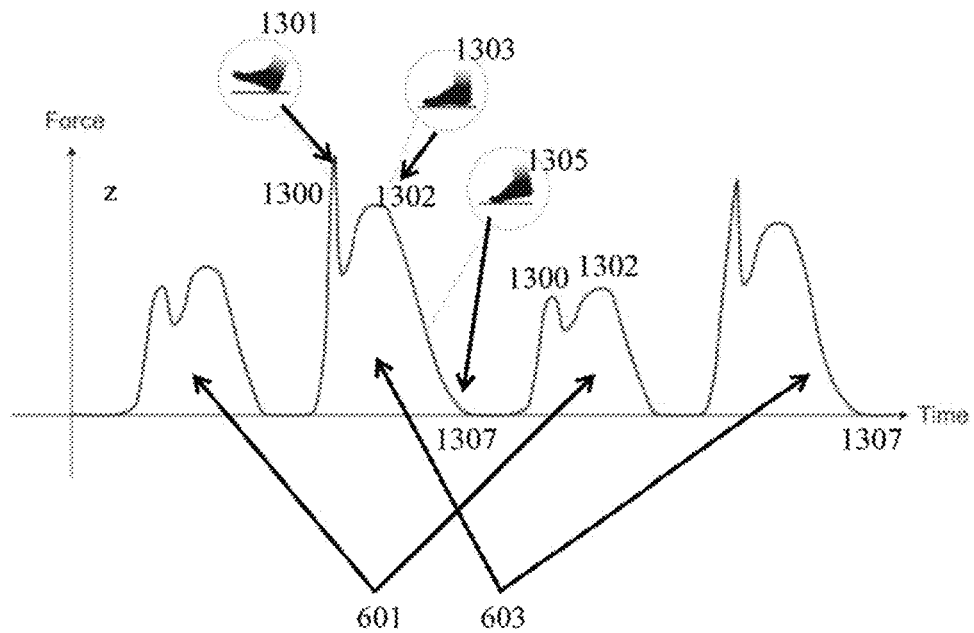
FIG. 13 shows the pattern of the landing force of a heel striker as monitored by the embodiment of FIG. 1.

FIG. 13 shows the pattern of the landing force of a heel striker. As in FIG. 7, the greater peaks 603 are forces detected in the steps of the leg on the same side of the user's body as the ear to which the present movement sensor is attached. The lesser peaks 601 are forces detected in the steps of the leg of the other side of the body. The force pattern shows an impact transient 1300 when the heel strikes the ground, at 1301, before a second peak 1302 which appears when the midfoot lands on the ground, at 1303. The force starts to diminish when the user rolls his weight onto the forefoot or the ball of his foot, at 1305, and finally no force is registered against the ground as the user lifts off the ground to take another step, at 1307.

Figure 14:
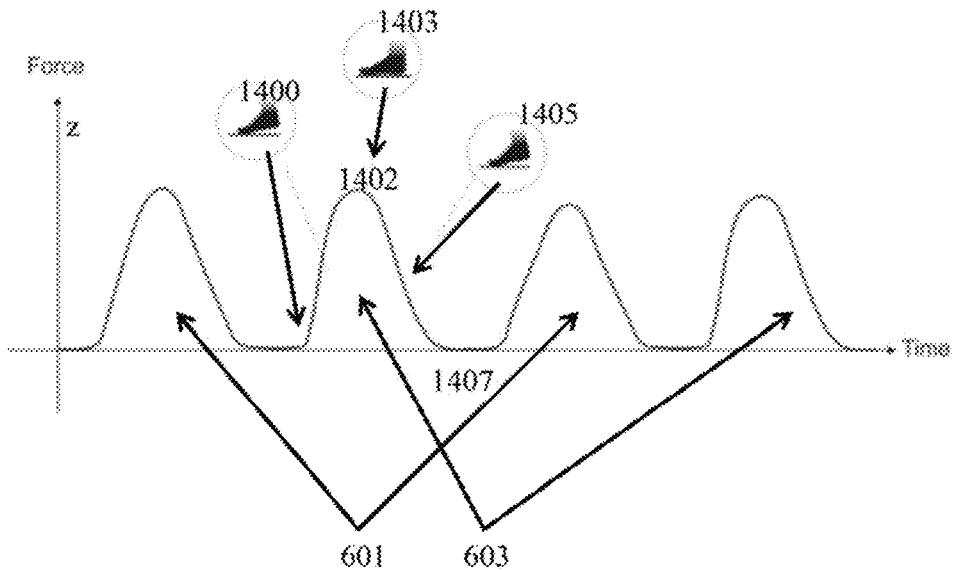
FIG. 14 shows the gentler pattern of the landing force of a forefoot striker as monitored by the embodiment of FIG. 1.

FIG. 14 shows the gentler pattern of the landing force of a forefoot striker. Forefoot landing does not produce a transient peak as shown in FIG. 13. The user lands on the ball of his foot, at 1400, which triggers a gentle increase in landing force 1401 against the ground detected by the movement sensor. The peak 1402 of the landing force appears when the midfoot hits the ground, at 1403. The landing force starts to diminish when the user rolls his weight back onto the forefoot, at 1405 and finally no force 1407 is registered against the ground as the user lifts off the ground to take another step, at 1407. The heel is not used to strike the ground at all. In some case, different shoes may change the strike type of running. In one of the embodiments, the force pattern is monitored the landing strike type with different type of shoes being worn. By comparing the landing strike type, one can determine which pair of shoes is most optimal for a user.

There is a trend for some people to re-train themselves to run with forefoot striking. However, it is difficult and takes time for a habitual heel striker to re-train himself to switch to forefoot striking as the feet and calf muscles needs to be strengthened. The gait monitor 100 as described can detect whether the user is landing on his forefoot or heel and issues alerts to the user to land on his forefoot when the habit of heel striking returns.

Figure 15:
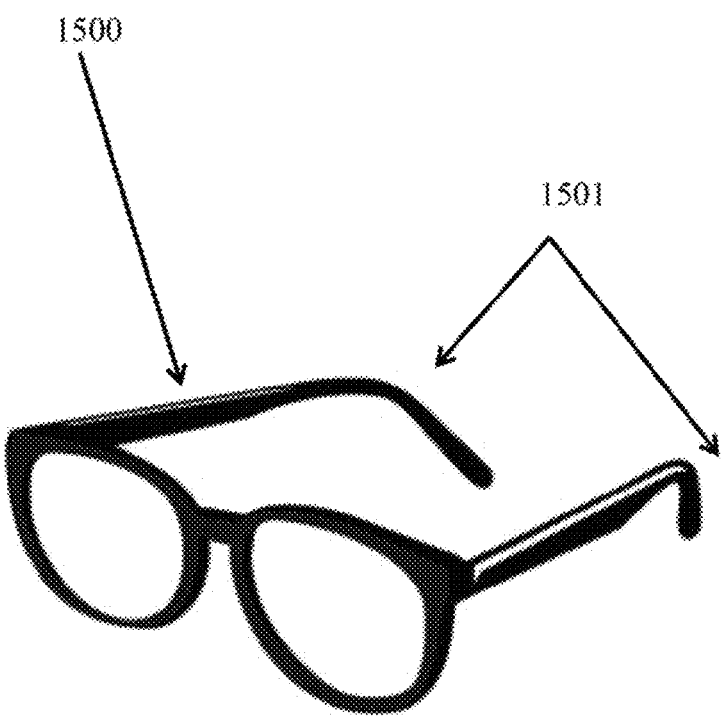
FIG. 15 shows an embodiment second to the embodiment of FIG. 1.
Figure 16:
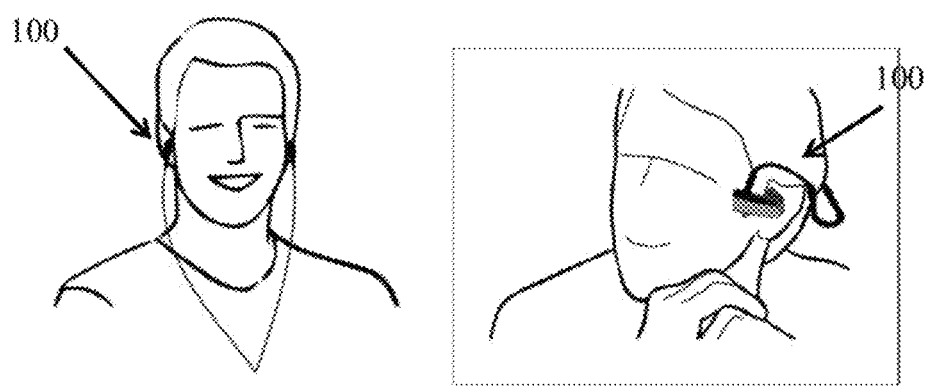
FIG. 16 shows further variations of the embodiment of FIG. 1.

A second embodiment 1500 is illustrated in FIG. 15 which is a pair of spectacles, glasses or goggles installed with a movement sensor in each of the temples 1501. The "temples" of the spectacles or glasses means the parts of the spectacles which are to be placed on or near the ear. The temples 1501 are considered sufficiently close enough to the joint of the atlas and axis vertebrae about which the head nods and the movement sensors will therefore experience little z-axis signal disturbance from the head nodding. In such embodiments, the feedback system is head mounting display on the spectacle frame, such as visual display on the lens of the spectacle which can be read by the wearer or a blinking LED light positioned near a hinge of the spectacle which can blink to alert the user of poor gait balance.

In a specific embodiment, the user may obtain an ear mountable movement sensor configured to monitor force patterns in the steps of the user from one supplier and another ear mountable movement sensor and use them in combination to monitor his gait.

The skilled man understands that other points on the body can be used which have left and right opposite mirror-image parts to which the movement sensors can be secured and which contributes relatively little noise due to bending or swaying of such parts. This may include the hip bone of the user which is subject to little sidewise sway during running and walking, except in the case of race walking. Relative one to the other, these left and right sides of the user's body are typically incapable of independent movements. Parts of the human body which is generally or roughly incapable of moving independently from the opposite counterparts are those such as the ears, the temples, left-right opposite positions on the jaw bone, left-right opposite positions on forehead, left-right opposite positions on the pelvis, hip bones, chest or ribs, teeth on the opposite sides of the jaw, the opposite corners of both eyes and so on. These parts of the body are usually located on the head or the trunk, and not in the limbs. These left and right parts of the body move generally in tandem, together, or one about the other, and do not move away or apart from the other in different directions. It is possible that some individual persons develop such body parts to be able to move one independently of the counterpart one, such as moving one ear and not the other, but this is an exception rather than the norm in normal body movements. These mirrored movements between the two parts provide a possibility of deducing the movements of a point or plane located in a plane of symmetry between the parts.

Some body parts such as the ears are capable of being moved along when the head tilts or turn. This may add additional readings to the movements detected from the user's gait. However, as both ears move together, use of two movement sensors makes it possible to identify movements resulting entirely from head tilting or turning, and allows one to negate their resultant readings by the movement sensors. In this way, any movements detected on any two of such counterparts which are generally incapable of relative motions may be used to monitor if a person has a tendency to skew towards one side of his body in the general.

In contrast, either one of limbs such as the hands, wrists or feet is capable of moving and flailing independently one of the other. For example, one hand may flail upwardly while the other hand downwardly. If the movement sensors are placed on the user's feet or hands, the readings obtained by these movement sensors will be unusable to estimate the skew of the midsagittal plane of the user, and therefore cannot measure gait as a matter of vertical misalignment or skew.

The skilled man understands that by the terms "earpieces, headphones", the embodiments may include all other manners of attachments to the ear in which movement sensors may be installed, including wireless Bluetooth ear pieces typically used for mobile phones and so on. FIG. 15 shows two of such embodiments 100 of the invention: the left side shows a man wearing an earphone which can be installed with the movement sensors as described, and the right side a man wearing a clipped on ear device shaped like the wireless Bluetooth earphone or like a hearing aid.

The skilled man understands that by the term "spectacle", all similar devices which can be worn over the eyes and ears such as goggles are included in the meaning.

Any forms of movement sensors may be used, such as gyroscopes, and the parameters monitored can be any one of angular changes, distance or velocity instead of acceleration. The readings of these movement sensors can be used to work out the force patterns in the steps of the user. However, it is preferable that embodiments do not use gyrometers for movement detection but use accelerometers in order to have a simpler movement sensor design with lower cost and longer battery life.

In some applications, such as in computer games which use accelerometers worn on the head as game controls, it may be necessary to determine the tilt angle of the user's head without needing lengthy calibration of the accelerometers to determine the tilt angle. For example, it would not be very acceptable to impatient garners if one has to carefully calibrate an accelerometer before it can be used in a game. The embodiments resolve this by using two accelerometers instead of a single accelerometer placed at the ears of the user.

Figure 17:
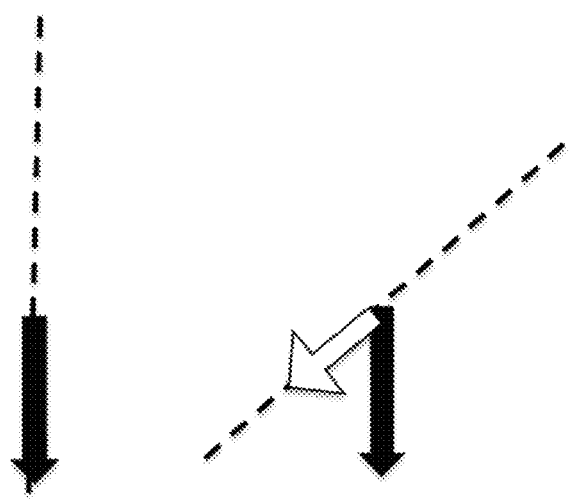
FIG. 17 shows a configuration of the embodiment using two movement sensors or accelerometers.

An accelerometer is typically capable of determining the direction to the ground or the perpendicular normal to the ground, which is according to the direction of gravity. If the axis of the accelerometer is aligned to the direction of gravity, and being momentously station the accelerometer will detect a I-G force in its vertical axis, i.e. the z-axis herein. However, if the accelerometer's z-axis is tilted away from the vertical line, the force detected along the z-axis will be lower. This is illustrated in FIG. 17. The left side of FIG. 17 shows the vertical or z-axis of an accelerometer aligned to the pull of gravity. The z-axis is represented by the dashed line and the direction of gravity represented by the black arrow. In this alignment, the accelerometer is able to detect gravity most strongly, as shown by the bigger arrow.

The right side of FIG. 17 shows the accelerometer tilted such that the z-axis of the accelerometer is placed at an angle to the normal, whereby detection of the force of gravity weakens as represented by the lesser white arrow. The white arrow also illustrates the projection of gravitational force when the z-axis of the accelerometer is titled. The black arrow in the right side of FIG. 17 represents the direction of gravity.

In other words, if the orientation of an accelerometer gives a 1G reading in the z-axis, it will be taken that the z-axis of the accelerometer is in line with the normal and therefore upright. Accordingly, the extent to which the z-axis reading reduce to less then 1G can be used to determine how much has the accelerometer tilted away from the normal by simple trigonometry.

Figure 18A:
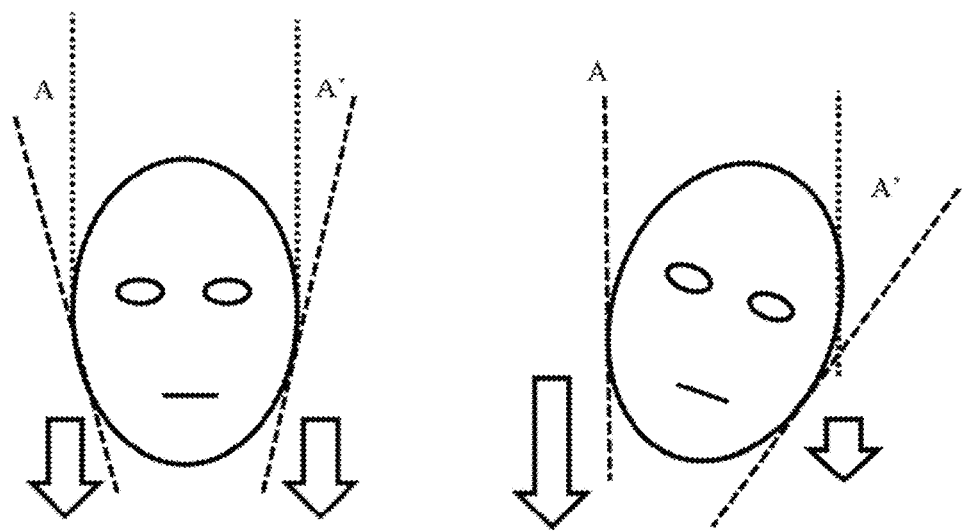
FIG. 18a shows the vector forces detected by two movement sensors when the user tilts his head sidewise.

The left part of FIG. 18a shows what happens when an accelerometer is worn in each ear of the user. The shape of the ear may cause a tilt in the accelerometer naturally, such that none of the two accelerometers has a z-axis aligned perfectly to the direction of gravity. The two arrows in the left side of FIG. 18a represent the detected acceleration by the two accelerometers in the direction of the normal. The arrows are actually falling short of the 1G force reading as none of the accelerometers registers a 1G reading, even though the head is held upright. Both accelerometers will detect a tilt because the ears cause them to be tilted. The tilt in the accelerometer caused by the shape of the ear is typically 0 to 45 degrees to normal.

If only one such tilted accelerometer were used, it would not be possible to resolve the tilting error easily. However, the embodiments use two accelerometers to estimate the direction of the normal.

The ears of a human are naturally shaped such that the angle formed between the z-axes of both the accelerometers widens towards the top of the user's head and converges towards his chin, in a somewhat symmetrical way. The angle detected by the rightward tilting of the left accelerometer and the angle detected by the leftward tilting of the right accelerometer should be approximately the same to the normal.

In FIG. 18a, "A" is the tilting angle detected by the accelerometer in the ear on the left side (right of the person in the picture). A' is the tilting angle detected by the accelerometer in the ear on the right (left of the person). A and A' are reference against the normal. The angle between the movement sensors is (A+A'). The true alignment of the user's head may be obtained by the following formula, which obtains the mean of the two angles:

$$(\text{Angle } A - \text{Angle } A')/2$$

Therefore, if the head is held upright, the mean of the two angles will be roughly aligned to the normal. There may be slight variation as the angle of tilt in both accelerometers caused by the ears may not be completely symmetrical.

The right side of FIG. 18a shows what happens when the user's head tilted towards the right of the page (left of the user). The accelerometer on the right side of the user detects a smaller force in the z-axis as it is even more misaligned to the normal, as indicated by the lesser arrow. This lesser angle is interpreted by the accelerometer as a greater angle A' away from the normal. The accelerometer on the left side of the user registers a greater force as it is more aligned with the normal, as indicated by the greater arrow. This greater arrow is interpreted by the accelerometer as a smaller angle A away from the normal, even a zero degree if perfectly aligned with the normal. The angle A and A' can be calculated by simple trigonometry.

Figure 18B:
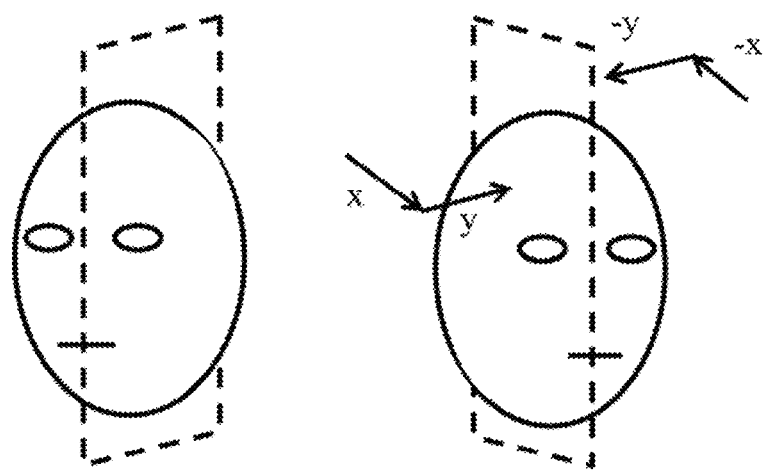
FIG. 18b shows the vector forces detected by two movement sensors when the user turns his head sidewise.

FIG. 18b shows the forces detected by both the accelerometers if the user turns or rotates his head from the upright front facing position to the right side of the drawing. The left accelerometer detects a forward x-axis force and a force in the y-axis rightward of the drawing. The right accelerometer detects a backward x-axis force and a y-axis force leftward of the drawing. The accelerometers do not normally detect any force in the x-axis and y-axis since there is no gravitational pull in the x-y plane. Only when there is movements in the x-y plane would force be detected. As human head cannot rotate 360 degree, it is not natural for a human head to rotate at a constant angular velocity.

Figure 18C:
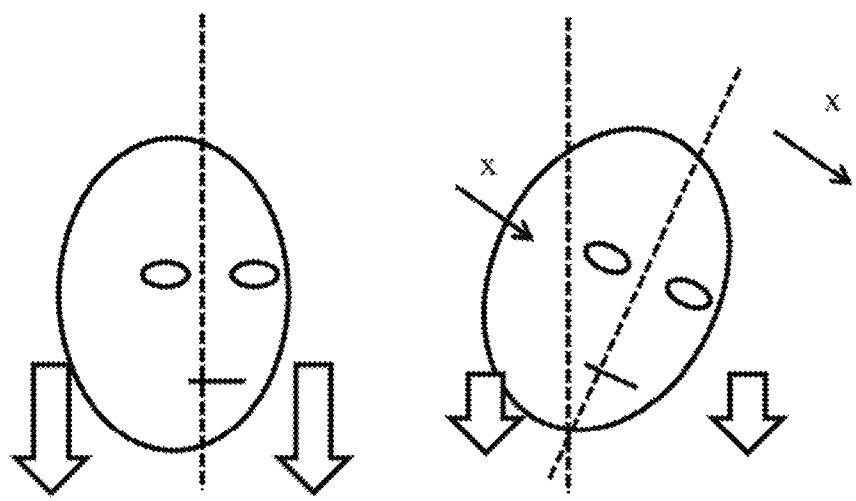
FIG. 18c shows the vector forces detected by two movement sensors when the user nods his head.

FIG. 18c shows the forces detected by both the movement sensors if the user tilts his head from the central, upright position to his front, as in nodding. Both movement sensors experience the same forward x-axis force. As both ears tilts away from the normal, the z-axis acceleration reading is reduced in both accelerometers. Therefore, it can be determined that forward nodding of the head causes both accelerometers to detect a similar change in force in the z-axis. Sidewise tilting of the head causes the accelerometers to detect a different change in force in the respective z-axis.

Accordingly, it is possible to detect different rotational head movements by using linear movement sensors such as accelerometers, and differentiate them from linear movements. With such detection, head movements may be used as an input for control devices.

In the prior art, rotation sensors such as a gyrometer is used to monitor the rotational movement. However, a gyrometer is energy intensive and requires a battery pack of sorts to supply power for its operation. In contrast, linear movement sensors, such as accelerometers are typically cheaper and require less power than gyrometers. For example, an accelerometer may be powered by several tens of micro-amperes, while a typical gyrometer consumes a few milli-amperes of current in the same amount of time.

Power requirements affect the physical size of wearable devices. Reducing current consumption allows a device to be powered entirely by energy harvest technology. Energy harvest technology refers to energy which is tapped from the user's or wearer's natural movements, body temperature or natural metabolic reactions, harvesting of solar energy or even radiofrequency energy in the air.

Accordingly, an embodiment using movement sensors such as accelerometers in place of gyrometers for monitoring user gait may be powered by a low current, reducing the need for high power batteries.

In another embodiment, a low power consumption movement sensor may be powered by electricity provided at the earphone or microphone jack of a mobile device, such as a mobile phone, for example. The current supplied at such a connector jack is typically provide less than 500 micro-Watt, which is insufficient to power a gyroscope but sufficient to power one or more movement sensors. Advantageously, this expands the usefulness of existing connector or connector jacks in conventional devices such as a mobile phone, and it is not necessarily a smart phone. A low power source such as the aforementioned microphone jack may now be used to supply power to a movement monitor, or gait monitor. Existing mobile phones do not need to be re-engineered to be useable with an expanded range of peripheral devices.

Figure 19A:
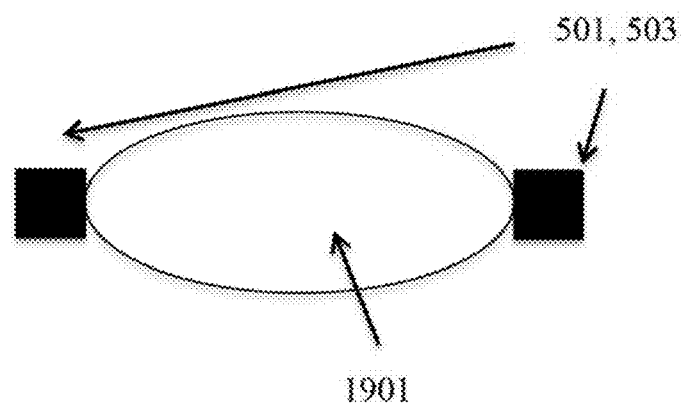
FIG. 19a shows another embodiment.
Figure 19B:
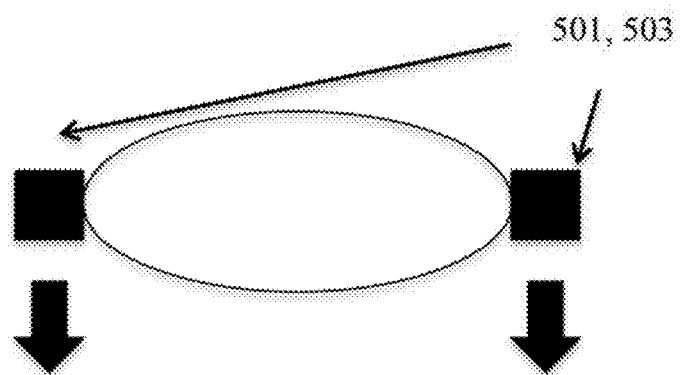
FIG. 19b shows the embodiment of FIG. 19a in movement.
Figure 19C:
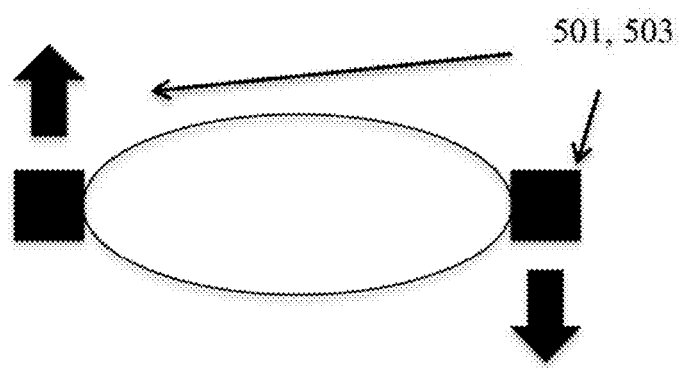
FIG. 19c also shows the embodiment of FIG. 19a in movement.

The foregoing embodiment can be applied to monitor the tilt of a device, such as the tilt of the surface of a watch, entirely powered by energy harvested from the wearer's body. This allows a watch, such as a smart watch, to be smaller and more compact while having sufficient ability to sense whether the user is looking into the smart watch screen. If the screen is generally level to the ground, this implies that the user is holding the watch in a position for reading the watch face. The smart watch then displays incoming messages for the wearer's eye. If the plane of the watch face is detected to be held perpendicular to the ground, incoming messages are not displayed. This safeguards privacy of information displayed on a smart watch. This is illustrated schematically in FIG. 19a to FIG. 19c, showing a disc representing the smart watch or any small planar device 1901. FIG. 19a shows the small device 1901 affixed with at least two accelerometers 501, 503 which are spaced apart from each other. It is preferable that the accelerometers 501, 503 are placed at opposite edges or sides of the device 1901 as, the further apart they are placed the more pronounced the difference in the movements detected by the accelerometers 501, 50 and, therefore, the more sensitive and accurate the detection of tilt. FIG. 19b shows how, if the device 1901 is moved in a leveled way and is not tilted, keeping the orientation of the planar surface of the device perpendicular to the direction of movement, the force detected by both the accelerometers 501, 503 will be the same. If the device 1901 is tilted, one accelerometer will register an upward force while the other will register a downward force, or one of the accelerometers detects a greater force than detected by the other accelerometer.

In one application, rotational of wrist-worn or handheld device can be used to scroll up and down the display on the device. An outward twist of the wrist can be used to scroll up the display on the smart watch, and an inward twist of the wrist can be used to scroll down the display on the smart watch. This relieves the user from having to use a finger of the other hand to touch the smart watch face to scroll through the watch display. Accordingly, use of two accelerometers in a smart watch provides the possibility of detecting whether the user is twisting his wrist quickly. Before this embodiment was conceived, it had been difficult to monitor wrist twisting without using a gyrometer and further reduce the power requirement of power sensitive devices such as watches.

In yet another embodiment, accelerometers or other kinds of movement sensors are mounted on the two sides of swimming goggles, swimming cap or swimming suit. The movement sensors are used to monitor the rotation movements of the swimmer and so detect the swimming style and his swimming efficient. In general, a swimmer's head and does not rotate much swimming in breast strokes, and but rotates side to side when swimming in free style. The amount of twisting of the body and head is indicative of the swimming efficiency of a swimmer. In this embodiment, advantageously, it is possible to harvest energy for powering the embodiment using water flow.

Although it has been described that tilting movement is monitored by two movement sensors, 501, 503, movements within a plane or rotational movements can also be monitored by the movement sensors 501, 503.

In some variations of the embodiments, more than two movement sensors may be applied. This may be to provide greater movement sensitivity. Instead of two movement sensors, for example, an array of three, four or more movement sensors may be provided at the edge of the device. Having more than two movement sensors prevents the malfunction of any one of the movement sensors from completely breaking down the tilt detection.

Figure 20:
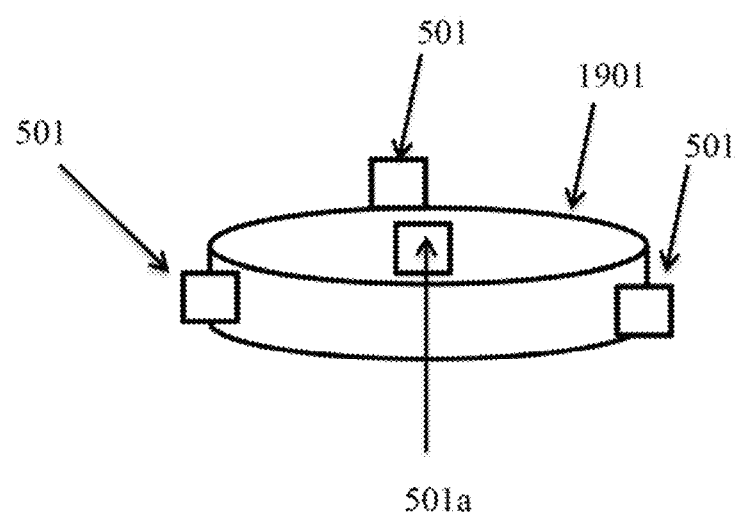
FIG. 20 shows yet another embodiment.

FIG. 20 schematically shows a round watch surface 1901 without the straps, lined with three movement sensors 501 around its edges. It is preferable that the movement sensors 501 are evenly distributed around the round watch surface 1901 but an uneven distribution is also possible, especially if there is a need to avoid watch straps, antennae (if the watch is a smart watch) and so on. A centrally placed movement sensor 501a is also provided for monitoring the overall movements of the watch surface, against which the readings of the movement sensors at the edge of the watch may be referenced for better determination of the movements and tilt of the watch.

Further embodiments may find application in control systems which require a turn of the hand or the wrist or some parts of the body, such as a wireless joystick, a wireless ring or set of rings to monitor the typing of a user and so on.

While there has been described in the foregoing description preferred embodiments of the present invention, it will be understood by those skilled in the technology concerned that many variations or modifications in details of design, construction or operation may be made without departing from the scope of the present invention as claimed.

For example, where accelerometers have been described, the skilled man understands other movement sensors are intended to be useable instead in other embodiments.

The invention claimed is:

1. A gait monitor, comprising
a pair of movement sensors in respective ear engagement portions of a headphone or earphone,
the pair of movement sensors configured to be worn on respective left and right ears of a user's body, wherein each of the pair of movement sensors detects movements of a respective side of the user's body; and
the gait monitor is configured to indicate skew of the midsagittal plane of the users body towards any one side of the user's body during movements of the user's body by regarding differences in force component readings between the pair of movement sensors.

2. The gait monitor as claimed in claim 1, wherein
a) each movement sensor is configured to monitor a z-axis being a vertical axis to ground, and an x-axis being a horizontal axis to the ground directed forward of the user's body and the gait monitor is configured to disregard detected movements comprising a z-axis force component concurrent with an x-axis force component, or
b) each movement sensor is configured to monitor a z-axis being a vertical axis to the ground, and a y-axis being a horizontal axis to the ground directed laterally of the user's body, and wherein the gait monitor is configured to disregard detected movements comprising a z-axis force component that is concurrent with a y-axis force component, or
c) each movement sensor is configured to monitor a horizontal axis to the ground and wherein the gait monitor is configured to disregard detected movements wherein one of the sensors detects movement in one direction and the other one of the sensors detects movement in an opposite direction.

3. The gait monitor as claimed in claim 1, wherein
the gait monitor is configured to determine if the force pattern indicates that the user lands on a heel of a foot of the user's body in steps of the user.

4. The gait monitor as claimed in claim 1, wherein
the gait monitor is configured to compare a force patter of left and right steps of the user detected by each of the pair of movement sensors.

5. The gait monitor as claimed in claim 1, wherein
a force patter of a step of the user is disregarded if a change in vertical force component in the step is accompanied by a concurrent change in a force component lateral to the user's body.

6. The gait monitor as claimed in claim 1, wherein
a force patter of a step of the user is disregarded if a change in a vertical force component in the step is accompanied by a concurrent change in a force component along a forward and backward direction to the users body.

7. The gait monitor as claimed in claim 1,
configured to compare force patterns of left and right steps of the user of the headphone or earphone to determine if the user has a balanced gait about the midsagittal plane of the user.

8. The gait monitor as claimed in claim 1,
configured to analyze a force pattern of steps of the user of the headphone or earphone to determine if the user has a heel strike or forefoot strike landing pattern.

9. The gait monitor of claim 1, wherein the pair of movement sensors are powered by energy harvested from the user when wearing the gait monitor.

10. A method of monitoring a gait of a person, comprising:
providing a headphone or earphone installed with a first movement sensor and a second movement sensor in respective ear engagement portions of the headphone or earphone,
attaching the first movement sensor to an ear of the person,
attaching the second movement sensor on the other ear of the person, and
obtaining a difference in readings of movement vectors between the movement sensors to indicate skew of the midsagittal plane of the user's body towards any one side of the user's body during movements of the users body.

11. The method of monitoring the gait of a person as claimed in claim 10, wherein the step of obtaining the difference in readings of movement vectors between the movement sensors is subject to:
a) disregarding movement vectors when a z-axis force component is accompanied by an x-axis force component, wherein the z-axis is an axis vertical to ground and the x-axis is an axis horizontal to the ground and forward of the person, or
b) disregarding movement vectors when a z-axis force component is accompanied by a y-axis force component, wherein the z-axis is an axis vertical to ground and the y-axis is an axis horizontal to the ground aligned to the person laterally, or
c) disregarding movement vectors in opposite directions in a horizontal plane.

12. A method of monitoring the gait of a person as claimed in claim 10, further comprising:
determining that a force patter shows that the person lands on ground by a heel strike; and
indicating to the person that the force patter shows that the person lands on the ground by a heel strike.

* * * * *